(12) United States Patent
Gariépy

(10) Patent No.: US 6,348,446 B1
(45) Date of Patent: *Feb. 19, 2002

(54) METHOD FOR SELECTIVELY PURGING CD77⁺ CELLS FROM BONE MARROW OR PERIPHERAL BLOOD

(76) Inventor: Jean Gariépy, 43 Chester Avenue, Toronto, Ontario (CA), M4K 2Z8

( * ) Notice: Subject to any disclaimer, the term of this patent is extended or adjusted under 35 U.S.C. 154(b) by 0 days.

This patent is subject to a terminal disclaimer.

(21) Appl. No.: 09/126,995

(22) Filed: Jul. 31, 1998

Related U.S. Application Data

(63) Continuation-in-part of application No. 08/599,211, filed on Feb. 9, 1996, now Pat. No. 5,801,145.

(51) Int. Cl.⁷ .............................................. C07K 14/25
(52) U.S. Cl. ...................... 514/12; 530/350; 530/402; 530/825; 930/200
(58) Field of Search ................. 514/12, 2; 530/350, 530/402, 825; 930/200

(56) References Cited

U.S. PATENT DOCUMENTS

| | | | |
|---|---|---|---|
| 4,831,122 A | 5/1989 | Buchsbaum et al. | 530/389 |
| 5,489,525 A | 2/1996 | Pastan | 435/7.23 |
| 5,503,981 A * | 4/1996 | Mueller et al. | 435/7.21 |
| 5,801,145 A * | 9/1998 | Gariepy | 514/12 |

OTHER PUBLICATIONS

Zhang, xg. Blood .83 (12): 3654–3663, 1994.*
Mechtersheimer, 6. Pathol Res Pract .186 (4): 427–438, 1990.*
Bray, MR. Proceed. Amzer. Assoc. 39: p 63, Mar. 1998.*
Shites D. et al. Medical Immunol. p. 11, 1993.*
Mangeney M et al. (1993) Cancer Research 53(21): 5314–5319.

Maloney M D et al. (1994) Journal of Experimental Medicine 180(1): 191–201.

Lacasse E C et al. (1996) 87ᵗʰ Annual Meeting of the American Association for Cancer Research 37(0): 184.

Lacasse E C et al. (1996) Blood 88(5): 1561–1567.

Farkas–Himsley, H. et al. (1995) Proc. Natl. Acad. Sci. 92: 6996–7000.

Junqua S. (1987) Eur J. Immunol. 17: 459–464.

A. Kalisiak et al. (1991) Int. J. Cancer 49: 837–845.

E. Oosterwijk et al. (1991) Int. J. Cancer 48: 848–854.

C. Ohyama et al. (1990) Int. J. Cancer 45: 1040–1044.

T. Ariga et al. (1991) Biochemistry 30: 7953–7961.

A. Cohen et al. (1990) International Immunology 2(1): 1–8.

* cited by examiner

*Primary Examiner*—Susan Ungar
*Assistant Examiner*—Minh-Tam Davis
(74) *Attorney, Agent, or Firm*—Ridout & Maybee

(57) ABSTRACT

A method for the selective purging ex vivo of CD77 positive cells from bone marrow or peripheral blood containing stem cells prior to autologous transplantation is described. The method involves treating the bone marrow or blood sample with shiga toxin or shiga-like toxin-1 to kill CD77⁺ cells or to remove them by affinity chromatography. The toxin selectively binds to CD77⁺ cells and not to other stem cells. The method offers a means for curing non-Hodgkin's lymphomas, myelomas and breast cancers expressing CD77.

11 Claims, 6 Drawing Sheets

//METHOD FOR SELECTIVELY PURGING CD77+ CELLS FROM BONE MARROW OR PERIPHERAL BLOOD

This application is a continuation-in-part of Ser. No. 08/599,211 filed Feb. 9, 1996, and which is now U.S. Pat. No. 5,801,145.

FIELD OF THE INVENTION

The invention is a method for the treatment of cancers such as non-Hodgkin's lymphomas (NHLs). The method utilizes shiga toxin or shiga-like toxin-1 to selectively kill cancer cells in bone marrow or peripheral blood ex vivo prior to reinfusion. The elimination of cancer cells by the method of the invention may provide a cure for some cancers.

BACKGROUND OF THE INVENTION

Shiga-like toxin-1 (SLT-1) is a bacterial toxin that, along with shiga toxin itself, binds to CD77, a cell surface glycolipid, and kills cells by inhibiting protein synthesis[1,2]. In the human hematopoietic system, CD77 expression is restricted to a subset of activated B cells[3-8].

Twenty thousand North Americans died of non-Hodgkin's lymphomas in 1994 alone. A large proportion of NHLs are follicular (B cell) lymphomas which are classified as low-grade lymphomas and for which no curative treatment exists[9]. Autologous bone marrow transplantation (ABMT) in patients with B cell malignancy is increasingly used as a therapeutic option. The transplanted marrow is frequently contaminated with residual cancer cells, which ultimately leads to a relapse of the patient. This contamination is a particular problem in relation to the treatment of follicular lymphomas; therefore, a safe and effective way of killing cancers cells, while sparing hematopoietic stem cells, is required for ABMT to become a useful and front-line therapy. Bacterial, plant and fungal toxins represents some of the most potent cytotoxic agents known; however, their toxicity cannot be exploited until such molecules can be targeted to specific cancer cells. A small subset of toxins in the context of an immunotoxin (antibody conjugate) or a fusion protein have been used in phase I or phase II trials in humans[10,11]. These toxin conjugates have met with limited success[12,13].

SUMMARY OF THE INVENTION

The invention provides a method for the ex vivo purging of bone marrow or peripheral blood containing stem cells prior to transplant using shiga toxin or shiga-like toxin-1 which binds specifically to the cell surface glycolipid CD77, so that all CD77-expressing cells in the bone marrow or blood sample are killed while the normal hematopoietic precursor cells are spared. The binding specificity of the toxin to the CD77 receptor can also be used to selectively remove CD77+ cells from bone marrow or blood samples using affinity chromatography.

The present invention preferably utilizes an unconjugated native bacterial toxin, shiga-like toxin-1 (SLT-1), as a chemotherapeutic drug in the ex vivo purging. For the purposes of the present invention SLT-1 functions equivalently to shiga toxin itself. SLT-1 is preferred because the expression system for this toxin is readily available[26]. Ex vivo purging avoids complications relating to the toxin's systemic toxicity. Severe combined immunodeficient (SCID) mice were used as recipients for SCID bone marrow seeded with the human Burkitt's lymphoma cell line, Daudi, as a model system for SLT-1 purging of B-cell NHL ex vivo. The SCID/Daudi model system has been well studied for in vivo experiments of B-cell immunotoxins[14,15].

DETAILED DESCRIPTION OF THE PREFERRED IMBODIMENT

SLT-1 Cytotoxicity

SLT-1 binds to a glycolipid present on colonic and kidney endothelial cells, called globotriosylceramide ($Gb_3$), which permits its internalization and leads to cell killing. This glycolipid is referred to as the CD77 antigen in the hematopoietic system and shows a restricted pattern of expression limited to a subset of activated B-cells in the germinal (follicular) center[3-5]. CD77 expression is prevalent in certain hematological cancers of B cells[6-8], such as Burkitt's lymphoma represented by the available cell line, Daudi. The sensitivity of Daudi cells toward the toxin was tested using purified SLT-1. The $IC_{50}$ dose for the toxin was found to be 1 pg/ml as measured by the cellular uptake of tritiated leucine (data not shown). To verify that the murine bone marrow cells demonstrated minimal toxicity toward SLT-1, bone marrow cells were cultured in an in vitro colony-forming assay in the presence or absence of toxin. The results presented in Table 1 show that the toxin was not toxic to the most primitive murine bone marrow precursor cells seen in this assay. A similar experiment with human bone marrow from a single acute myelogenous leukemia (AML) patient also showed little toxicity at high doses (Table 1).

TABLE 1

In vitro toxicity of Shiga-like toxin-1 against murine and human bone marrow cells

| | murine | | | human | | |
|---|---|---|---|---|---|---|
| SLT-1 conc | $E_{mix}$ (CFU) | CFU-GM + $E_{Meg}$ (CFU) | Total CFUs | CFU (day 7) | BFU-E (day 16) | CFU-C (day 16) |
| 0 | 4 | 70 | 74 | 67 | 36 | 55 |
| 1 ng/ml | 4 | 66 | 70 | ND | ND | ND |
| 10 ng/ml | 4 | 57 | 61 | 66 | 30 | 60 |
| 100 ng/ml | 4 | 54 | 58 | 45 | 20 | 60 |

TABLE 1-continued

In vitro toxicity of Shiga-like toxin-1 against murine
and human bone marrow cells

|  | murine | | | human | | |
| --- | --- | --- | --- | --- | --- | --- |
| SLT-1 conc | $E_{mix}$ (CFU) | CFU-GM + $E_{Meg}$ (CFU) | Total CFUs | CFU (day 7) | BFU-E (day 16) | CFU-C (day 16) |
| 1000 ng/ml | 4 | 41 | 45 | 52 | 20 | 50 |
| 10 µg/ml | 4 | 39 | 43 | ND | ND | ND |

Abbreviations: $E_{mix}$ represents cells that gave rise to colonies with progenitor cells from at least three different morphological types including erythroid cells, referred to as mixed erythroid colonies. CFU, colony-forming unit; CFU-GM + $E_{meg}$ is the sum of CFU-granulocyte/monocyte and erythroid/megakaryocyte colonies; Total CFUs represent the sum of $E_{mix}$ and CFU-GM + $E_{Meg}$; BFU-E, burst forming unit-erythroid; CFU-C, colony forming unit in culture. ND, not determined.

SLT-1 Effect on Immune Reconstitution

Figure 1:
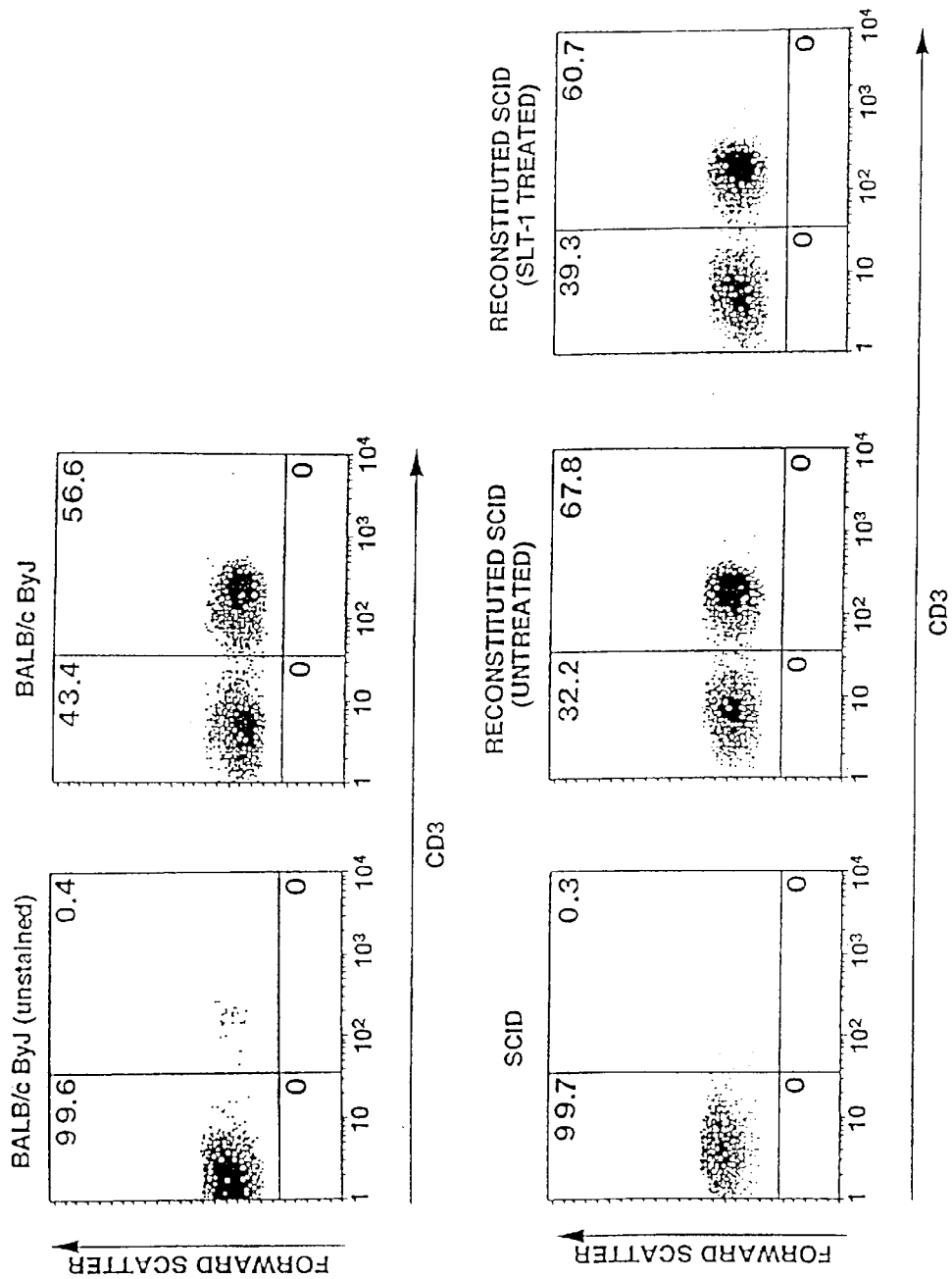
FIG. 1 shows flow cytometry results of the detection of mature T cells (CD3+) in peripheral blood of reconstituted SCID mice at 10 weeks after bone marrow transplant compared to control mice.

Next, SLT-1-treated or untreated bone marrow cells were transplanted into irradiated SCID mice to verify their reconstitution in an in vivo setting. SCID mice lack circulating mature B and T cells. Bone marrow from an immunocompetent 'congenic' strain of mouse (BALB/c ByJ) was treated or not with SLT-1 in vitro and used to reconstitute SCID mice. The appearance of mature B and T cells, indicative of reconstitution by BALB/c ByJ bone marrow precursors, was monitored by flow cytometry using antibodies to CD3 (T cells) and B220/CD45R (B cells). SCID mice transplanted with the BALB/c ByJ bone marrow had a reconstituted immune system at 10 weeks post-transplant (FIG. 1) since their CD3 profiles (68%) were the same as that of a BALB/c ByJ mouse control (57%). No obvious differences could be observed in the percentages of T cells in the reconstituted mice that had received marrow after SLT-1 treatment (61%) or no treatment (68%). Evidence of reconstitution of the B cell lineage was similarly confirmed by flow cytometry (B220/CD45R; data not shown).

SLT-1 Purging of Human Lymphomas ex vivo

Figure 2:
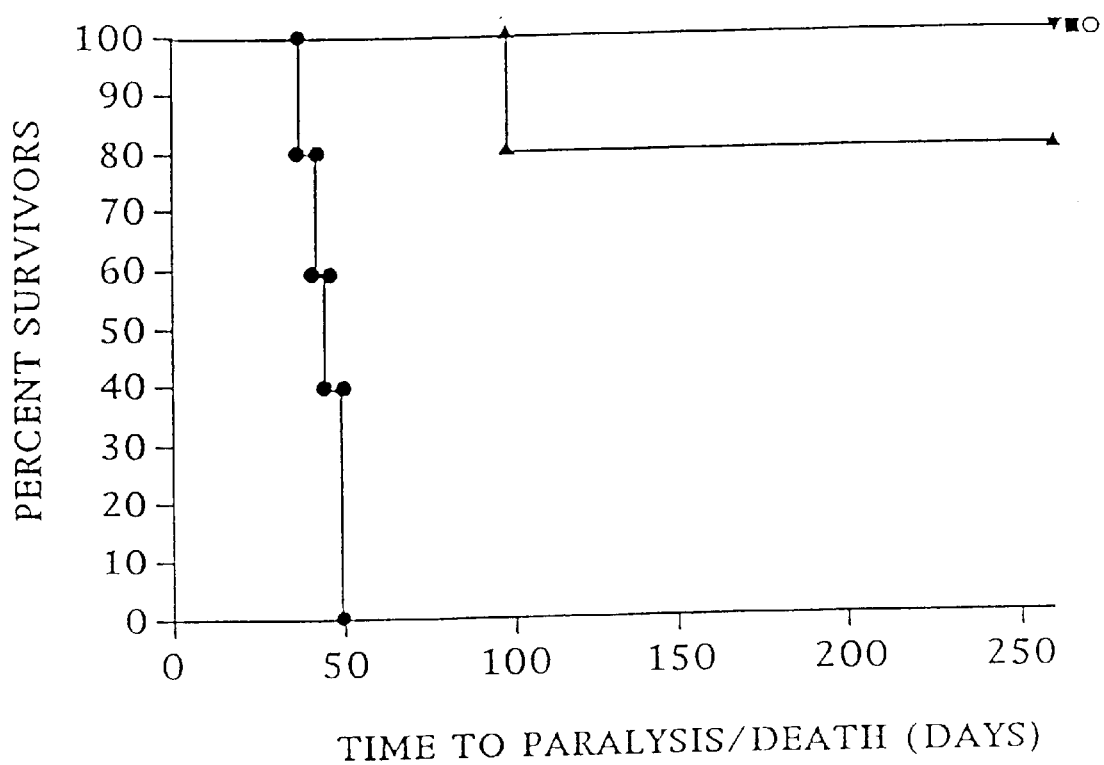
FIG. 2 is a Kaplan-Meier plot of the disease-free survival of SCID mice transplanted with bone marrow purged according to the invention.

Purging experiments were then initiated in SCID mice which served as a transplant host for the human xenograft. This model has a well-defined endpoint, i.e., hind-leg paralysis of SCID mice due to the dissemination and invasion of the spinal cord by the lymphoma[14, 15]. Bone marrow was harvested from SCID mice, seeded or not seeded with Daudi cells (33% of total cells which represents a high tumor burden), purged with or without 10 ng/ml of SLT-1 for 60 min at 37° C., washed and injected into irradiated SCID mice. Mice were examined daily for signs of disease and the period of disease-free survival (paralysis-free) noted. Disease-free survival was plotted as the time to paralysis of SCID mice transplanted with Daudi cells ($1\times10^6$) treated with or without 10 ng/ml SLT-1 (37° C., 60 min). Mice were injected via the tail vein with either bone marrow cells (sterility control, ▼), or bone marrow cells seeded with Daudi cells (positive disease control, ●), or with SLT-treated bone marrow (washing control, ■), or with SLT-treated bone marrow and Daudi mix (purged marrow/treatment group, with ○ or without toxin-neutralizing antibody, ▲). One of the purging groups (SLT-treated Daudi cells, ○) was mixed with a toxin-neutralizing polyclonal antibody[30] (100 µl of antisera for 200 µl of cells) after treating the bone marrow with the toxin but prior to injection. One mouse out of ten in the purged groups died on day 98 (▲). This animal showed no signs of paresis or paralysis. Its death was attributed to natural causes, although the cancer can not be ruled out as a cause of death. The Kaplan-Meier plot (FIG. 2) illustrates the rapid onset of cancer symptoms (paralysis at days 38–49) for the longest running experiment for the group of mice injected with bone marrow and 1 million untreated Daudi cells (disease control). The purging of Daudi-contaminated bone marrow with SLT-1 has lead to a large increase in disease-free survival (and cure), as this group was still alive and disease-free 9 months past the disease control group median period for disease-free survival.

Expression of SLT-1 Receptor on Lymphoma and Myeloma

Figure 3:
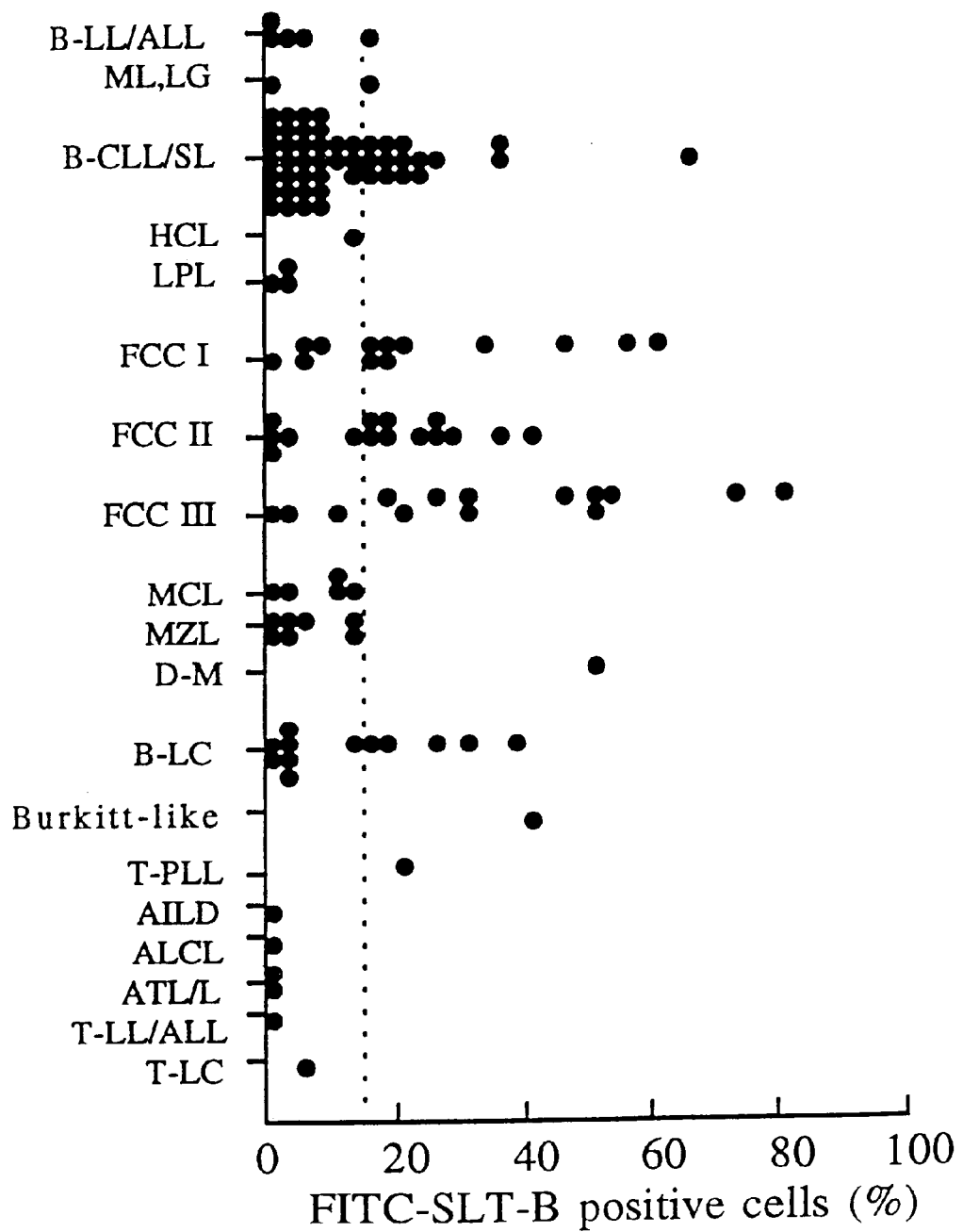
FIG. 3 is a graph showing the detection of CD77+ cells in human hematological cancers.
Figure 4:
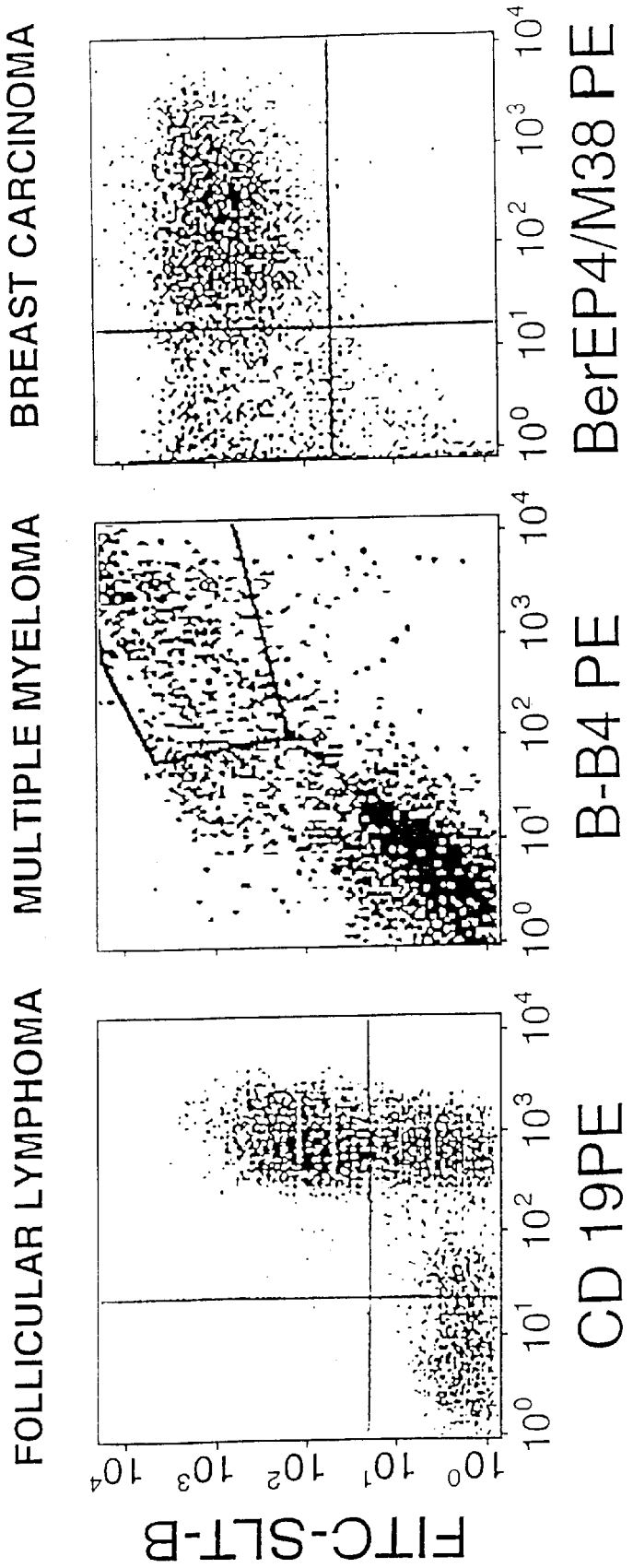
FIG. 4 shows flow cytometry results of the detection of SLT-1 receptors on follicle centre lymphoma, multiple myeloma, and breast carcinoma.

Clinical samples from patients with leukemia and lymphoma were routinely screened with FITC-SLT-B fluorescein isothiocyanate labeled SLT-1 B-subunit to identify SLT-1 receptor expression on and flow cytometry data collected on 134 sequential samples (FIG. 3). On average, 3% of cells (+/−4%) recovered from non-malignant samples stained with the fluorescent probe. Clinical samples were scored as positive when at least 15% of cells (3 SD's above the mean background) bound FITC-SLT-B. SLT-1 receptors were frequently expressed on follicle centre cell lymphoma grades I, II and III (FIG. 3) with 31 of 43 (72%) patient samples positive. These results agree with the expression of CD77 on normal follicle centre cells. Thirty-three percent (15 of 46 samples) of small lymphocytic lymphomas with or without chronic lymphocytic leukemia were positive for FITC-SLT-B staining, as were 42% (5 of 12 samples) of large B-cell lymphomas. FITC-SLT-B staining was not observed on mantle cell lymphomas which are thought to arise from the normally CD77 negative B-cells in the follicular mantle zone. Marginal zone lymphomas were also CD77 negative. The B-cell acute lymphocytic leukemias were essentially CD77 negative. Flow cytometry (2 samples) and immunohistochemistry (5 samples) were performed on bone marrow aspirates collected from multiple myeloma patients. The marker syndecan-1, identified by the antibody B-B4 was used to detect normal plasma cells as well as multiple myeloma cells. Normal plasma cells were found to be syndecan-1$^+$, CD77$^-$, while samples from multiple myeloma patients investigated were syndecan-1$^+$, CD77$^+$ (FIG. 4). Abbreviations: LL/ALL, B; B-cell lymphoblastic lymphoma/acute lymphoblastic leukemia; LL/ALL, T; T-cell lymphoblastic lymphoma/acute lymphoblastic leukemia; ML, LG; malignant lymphoma, low grade (non-classifiable); SL+/−CLL, small lymphocytic lymphoma with or without chronic lymphocytic leukemia; HCL, hairy cell leukemia; SL-P, small lymphocytic, plasmacytoid; FCC-I, follicular-small cell cleaved; FCC-II, follicular-mixed; FCC-III, follicular-large cell; MZ; marginal zone lymphoma; D-M, diffuse-mixed; D-LC, diffuse-large cell; T, IG-LC, T-cell intermediate grade large-cell lymphoma; SNCC, small non-cleaved cell; T, PLL, T-lymphocytic, prolymphocytic leukemia; T, ALCL, anaplastic large cell lymphoma; T, ATL/L, adult T cell lymphoma/leukemia; T, AILD, angioimmunoblastic T-cell lymphoma. Patients with diffuse large cell lymphoma who had a documented history of follicle centre cell lymphoma were included in the FCC-III category.

Expression of SLT-1 Receptor on Breast Cancer Cell Lines and SLT-1 Cytotoxicity

The expression of SLT-1 receptors on 18 breast cancer cell lines was analyzed by flow cytometry using FITC-SLT-B. Two antibodies were used to label breast cells: Ber-EP4 which recognizes an unknown epithelial antigen on epithelial-derived carcinomas, and M38 which detects the epitope MUC1 on breast-derived mucin. Of the 18 breast cancer cell lines studied, five had less than 15% positivity for FITC-SLT-B while 13 (72%) expressed surface SLT-1 receptors (Table 2). 16 of 18 (89%) breast cancer cell lines were positive for M38 (MUC1) and 13 of 18 (72%) were positive for Ber-EP4. The results demonstrate the frequent expression of SLT-1 receptor on the surface of breast cancer cell lines. The level of expression of SLT-1 receptor on breast cancer cell lines is correlated with their sensitivity to killing by SLT-1 (Table 2, $CD_{50}$ values).

LTBMC and cobblestone assays, both of which depend on formation of a stroma. Flow cytometry identified a population of $CD10^+$, $CD13^+$, $CD77^+$ stromal cells (data not shown). These cells were further characterized by single and dual immunocytochemical staining of stromal cells grown directly on plastic slides and confirmed the presence of CD77 on a fibroblast-like cell that was $CD10^+$, $CD13^+$ and

TABLE 2

Human breast cancer cell line surface antigens and SLT-1 sensitivity

| Cell lines | Dx | SLT-R | Ber-EP4 | M38/MUC1 | CD50 values |
|---|---|---|---|---|---|
| Hs578T | CAR | − | − | ++ | ND |
| MDA-MB-330 | LOB | − | − | − | ND |
| MDA-MB-468 | IDC | − | − | +++ | >10 μg/ml |
| CAMA-1 | AC | − | +++ | +++ | >10 μg/ml |
| BT-474 | IDC | − | +++ | +++ | ND |
| BT-20 | IDC | + | − | + | ND |
| DU4475 | MET (skin) | + | +++ | +++ | ND |
| MDA-MB-134 | IDC | + | +++ | ++ | ND |
| MDA-MB-435S | IDC | + | − | ++ | ND |
| ZR-75 | IDC | + | ++ | +++ | ND |
| MCF-7 | IDC | +/++ | +++ | ++/+++ | 2 ng/ml |
| MDA-MB-157 | MED | ++ | +++ | +++ | ND |
| SKBR3 | AC | ++ | +++ | ++/+++ | >10 μg/ml |
| JS-1 | MET (bone) | ++ | − | − | 40 ng/ml |
| MDA-MB-231 | AC | +++ | + | +++ | 0.01 ng/ml |
| MDA-MB-469 | ND | +++ | +++ | +++ | 0.01 ng/ml |
| T47D | IDC | +++ | +++ | +++ | 0.7 μg/ml |
| UACC-812 | IDC | +++ | +++ | +++ | ND |

Abbreviations: Dx, morphological diagnosis (64); CAR, carcinosarcoma; LOB, lobular carcinoma; IDC, intraductal carcinoma; MET, metastastic carcinoma; MED, medullary carcinoma; AC, adenocarcinoma; $CD_{50}$, dose of SLT-1 required to kill 50% of cells; ND, not determined; expression of surface antigen in terms of percentage of cells staining positively for a marker: defined as negative or '−' (0–14%), weak or '+' (15–40%), intermediate or '++' (41–70), and strong or '+++' (71–100%).

Expression of SLT-1 Receptor on Breast Cancer Biopsies

The expression of SLT-1 receptor on biopsies of primary human breast cancers obtained from 10 patients was analyzed by flow cytometry and immunocytochemistry. Cell suspensions were prepared from fine-needle aspirates or by mechanical disaggregation of solid tumors. Eight of 10 samples (80%) showed greater than 15% positive staining for FITC-SLT-B (Table 3) and the intensity of fluorescence staining was high (FIG. 4). In contrast to the established breast cancer cell lines, Ber-EP4/M38 was expressed on 3 of 9 samples, all of which were positive for SLT-1 receptors. Four of seven SLT-R+ samples were negative for the breast cancer markers (Ber-EP4, M38) but the SLT-1 receptor positive cells were confirmed as breast cancer cells by morphology, and cytospin immuno-cytochemistry with anti-low molecular weight cytokeratin antibodies and anti-CD77.

Effects of SLT-1 on Long-term Bone Marrow Cultures and CD77 Expression of Bone Marrow Stromal Cells Long-term bone marrow cultures, LTBMC were performed to investigate the toxicity of SLT-1 against hematopoietic stem cells. LTBMC were established after 30 min. incubation of SLT-1 (10 ng/ml or 1 μg/ml) with bone marrow from 5 normal donors and one breast cancer patient. Unbound toxin was removed from the treated samples before plating cells into long-term culture conditions. At two week intervals, half of the cell suspensions was withdrawn and plated into short term methylcellulose assays to analyze colony formation. A confluent layer of stromal cells normally forms over the first few weeks of culture and provides growth support for the suspended or lightly adherent hematopoietic cells. SLT-1 however inhibited the growth and formation of a stromal layer and compromised the alkaline phosphatase positive. These cells were identified as $CD77^+$ cells of mesenchymal origin, similar to the flat angulated $CD10^+$ stromal cell or the LTBMC adherent $CD10^+$, $CD13^+$ cell which appears here to have osteogenic potential (alkaline phosphatase activity).

TABLE 3

Breast cancer biopsy surface antigens

| Biopsies | Dx | SLT-R | Combined Ber-EP4/M38 | LMWK |
|---|---|---|---|---|
| BC-1 | IDC | +/++ | +/++ | ND |
| BC-2 | IDC | ++ | ++ | ND |
| BC-3 | IDC | + | − | ND |
| BC-4 | ILC | ++ | − | ND |
| BC-5 | IDC | + | − | + |
| BC-6 | ILC | + | − | + |
| BC-7 | IDC | ++ | ++ | + |
| BC-8 | IDC | − | − | ND |
| BC-9 | ILC | − | − | ND |
| BC-10 | IDC | +++ | +++ | ND |

Abbreviations: Dx, morphological diagnosis; IDC, invasive ductal carcinoma; ILC, invasive lobular carcinoma; expression of surface antigen in terms of percentage of cells staining positively for a marker: defined as negative or '−' (0–14%), weak or '+' (15–40%), intermediate or '++' (41–70%), and strong or '+++' (71–100%); LMWK, low molecular weight keratins detected by immunohistochemistry, expression is defined as negative (−) or positive (+) only; ND, not determined.

Effects of SLT-1 on $CD34^+$ Stem Cells and ex vivo Lymphoma Purging

Figure 5A:
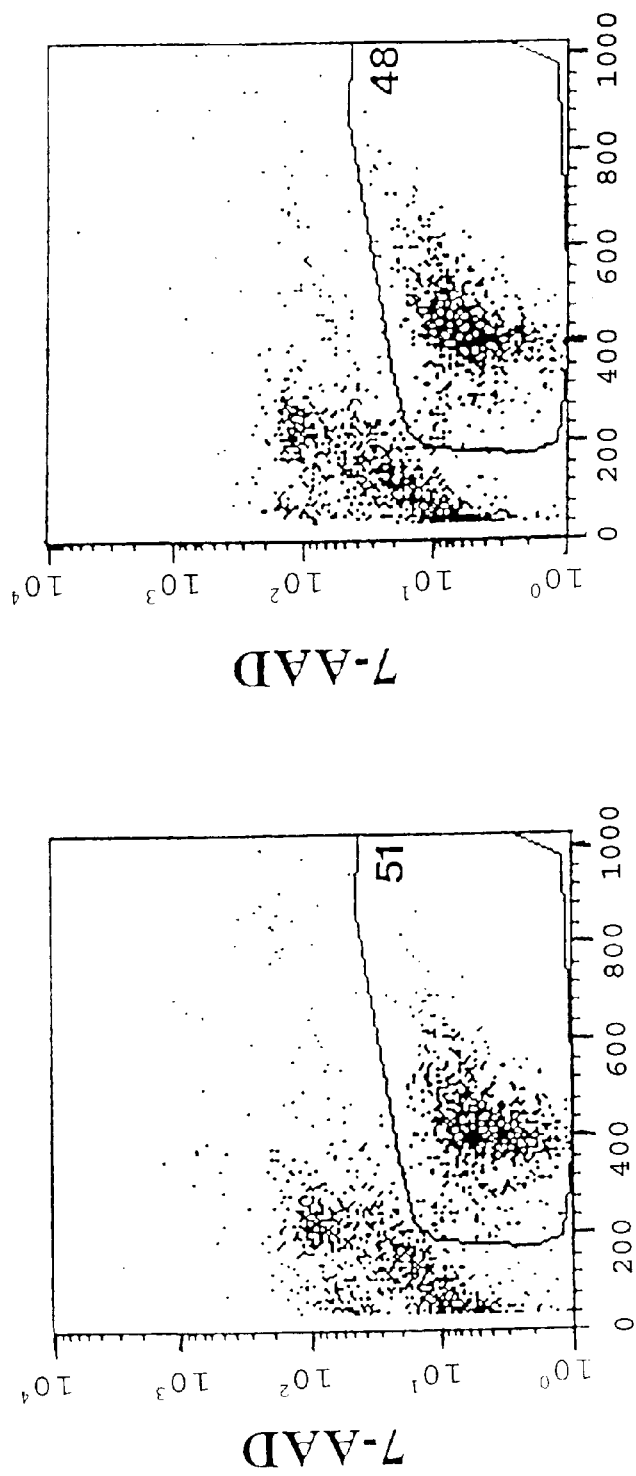
FIGS. 5A and 5B show flow cytometry results of the effect of SLT-1 on CD34+ peripheral blood stem cells and in purging of CD77+ B lymphoma cells.
Figure 5B:
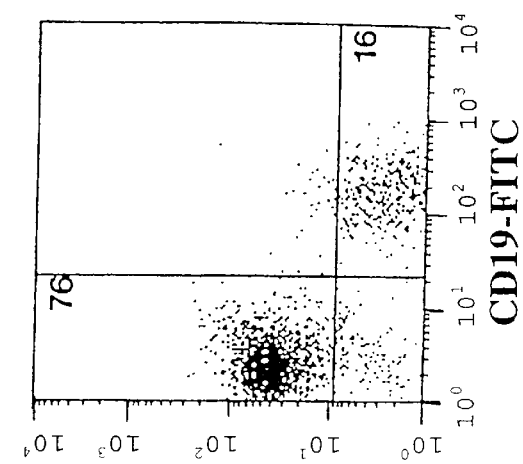
Figure 5B:
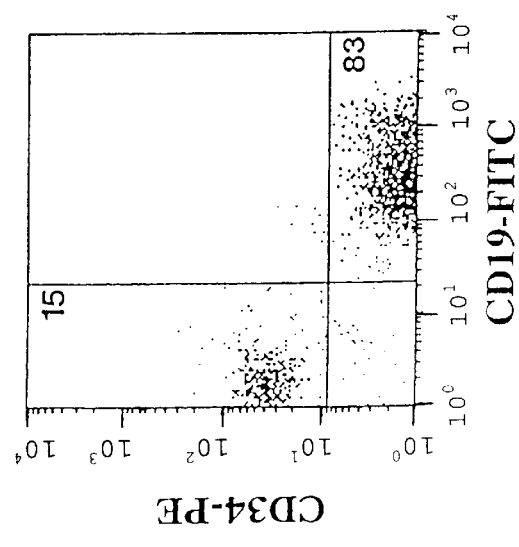
Figure 5B:
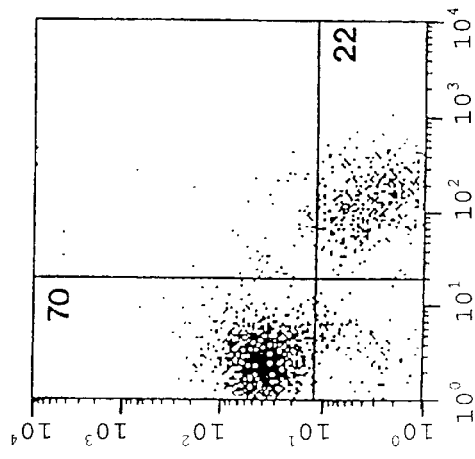
Figure 5B:
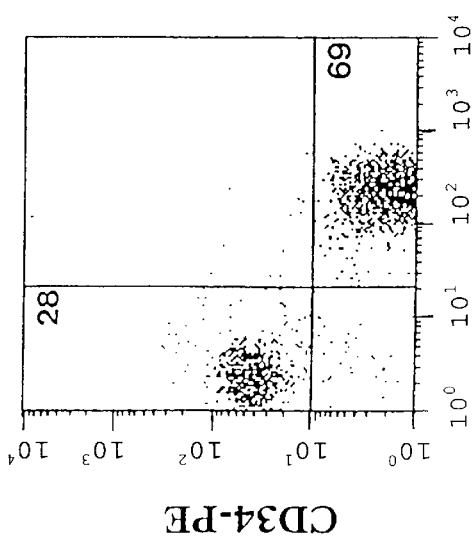

The toxicity of SLT-1 was investigated by culturing purified human $CD34^+$ stem cells and early committed progenitors in the presence or absence of a high dose of SLT-1 (1 $\mu$g/ml) for 2 days and measuring cell viability by flow cytometry (light scattering and 7-AAD (7-amino actinomycin D) dye exclusion). After two days culture there was no difference between the number of viable $CD34^+$ cells found in toxin-treated (48%) and untreated $CD34^+$ cell samples (51%) (FIG. 5A). The 50% loss of viability occurring in both samples is due to spontaneous apoptosis in the culture system. A second experiment was designed to mimic purging of peripheral blood stem cells contaminated with $CD19^+$, $CD77^+$ Burkitt's lymphoma cells. Purified peripheral blood stem cells ($CD34^+$, $CD19^-$) were mixed 1 to 1 with a $CD19^+$ Daudi, Burkitt's lymphoma cell line, cultured for 2 days with or without 1 $\mu$g/ml of SLT-1, and the viability of both populations were analyzed simultaneously by flow cytometry. The Burkitt's lymphoma cell line cultured without SLT-1 continued to proliferate and exceeded the number of $CD34^+$ cells by 5-fold (83% to 15%, FIG. 5B, bottom panel), but in the presence of toxin, the ratio of $CD19^+$ tumor cells to $CD34^+$ stem cells was reversed (16% to 76%), demonstrating the specific purging effect of the toxin towards $CD77^+$ tumor cells and the lack of effect against $CD77^-$, $CD34^+$ stem cells. The differential killing of CD77 positive cells is greater than is documented in this 2-day incubation as the cell death induced by SLT-1 manifests maximally 3 to 4 days post-intoxication.

Discussion

An important criteria for using SLT-1 in bone marrow purging experiments is that bone marrow progenitors show no or little sensitivity to the purging agent even at high doses. Treatment of murine bone marrow with even 10 $\mu$g/ml of SLT-1 ($10^7$ times the $IC_{50}$ dose for Daudi cells) resulted in only a small reduction in the number of colonies. This was expected as CD77 expression has not been detected in human bone marrow by immunochemistry[16], nor have human bone marrow precursor cells shown any alarming toxicity to SLT-1 ($IC_{50}$>1 $\mu$g/ml) in vitro[17]. SLT-1 toxicity against bone marrow precursor cells was also tested in a setting (immune reconstitution) that more closely resembles the ABMT procedure. FACS analyses (FIG. 1) illustrate that peripheral blood from control SCID mice had virtually no CD3-positive cells[18] while a control BALB/c ByJ had a large percentage of CD3-positive cells (57%) for the lymphocyte gated-population, as expected. The lymphocyte population in BALB/c ByJ or reconstituted SCID mice was 58–65% of the total mono-nuclear cell population in comparison to only 16–17% for age-matched control SCID mice (data not shown). This finding agrees with values of differential counts of leukocytes in the peripheral blood of SCID mice and immunocompetent C.B-17 mice[19] and demonstrates the safety of using SLT-1 as a purgative.

The Burkitt's lymphoma cell line, Daudi, was chosen as a model for NHL. The appearance of cancer symptoms (FIG. 2) in the mice agrees with expected results[14, 15]. The implantation of only 100 Daudi cells has been shown to give rise to hind-leg paralysis by about day 90 (mean survival time)[14, 15]. The injection of $10^6$ SLT-1-intoxicated Daudi cells has thus resulted in a tripling of the mice disease-free survival period, which suggests that at least 4 logarithmic units of Daudi cells have been purged from the bone marrow. The experiment has been repeated twice more with similar results.

A direct approach to testing SLT-1 action on peripheral blood stem cells was taken by culturing purified human $CD34^+$ cells with or without SLT-1. The viability of $CD34^+$ cells was not affected by the toxin (FIG. 5A). To confirm that the toxin retained its biological activity, it was used to kill $CD77^+$ lymphoma cells mixed with $CD34^+$ cells (FIG. 5B). The present findings indicate a lack of toxicity of SLT-1 against $CD34^+$stem cells. This conclusion is further supported by the known restricted expression patterns of CD77, which is not found on $CD34^+$ cells, early committed progenitors or circulating B- and T-cells.

Previous work by other groups identified the tissue and cell distribution of CD77 on normal and neoplastic tissues using antibodies[3-8, 16, 20, 21]. Since the structural determinants of CD77 recognized by monoclonal antibodies are likely different than those recognized by the toxin itself, probing experiments were conducted with the toxin B-subunit for the presence of SLT-1 receptors on human cells derived from cancer patients that might benefit from ABMT. These results emphasize the prevalence of this marker for MLs, especially follicular lymphomas, and its virtual absence from other hematological (myeloid) cancers and normal samples. This finding agrees with previous results using anti-CD77 antibodies which demonstrate a high frequency (~60%) of expression for NHL[6]. The skilled person will appreciate that the B-subunit of shiga toxin can be attached to a resin and employed to selectively remove $CD77^+$ cells from a cell mixture. Thus, instead of killing $CD77^+$ cells using shiga toxin or SLT-1, it may be advantageous in certain applications to selectively remove $CD77^+$ cells from bone marrow using affinity chromatography with bound B-subunit of shiga toxin.

SLT-1 represents an ideal purging agent for the following reasons. It is cytotoxic throughout the cell-cycle[22] and differs in cell-cycle dependence patterns from that of conventional chemotherapeutic drugs. It possesses an impressive ability to eliminate clonogenic tumor cells (greater than the detection limit of the assays used here, i.e., >4–5 log units of cell killing). It shows no toxicity against normal bone marrow progenitors, sparing stem cells. It is very soluble in most aqueous media and can be easily removed prior to reinfusion. Finally, it possesses a theoretical lack of cross-resistance with prior in vivo drug regimens because of its distinct mode of action. In fact, SLT-1 may potentiate the action of conventional drugs, as is the case for immunotoxins[13].

The method of the invention has demonstrated in an animal model that treatment of a lymphoma with a single biological agent ex vivo can result in a cure. To date, combinations of immunotoxins with or without additional chemotherapeutic drugs have been required to achieve potentially similar results[15,23,24]. The presence of SLT-1 receptor on breast cancer, follicle centre cell lymphoma and multiple myeloma cells and lack of toxicity of SLT-1 towards $CD34^+$ stem cells suggests a potential for SLT-1 as an ex vivo purging agent in removing tumor cells from autologous stem cell transplants of breast cancer, lymphoma and myeloma patients.

Methodology

Colony Forming Assays

Murine bone marrow cells were obtained from untreated SCID mice by flushing femora and tibiae with Iscove's modification of DMEM medium (IMDM) and 5% fetal calf serum (FCS) using a 25-gauge needle. Bone marrow cells were then put into semi-solid 1% methylcellulose (a gift from Shin-Etsu, Japan) cultures in IMDM medium lacking HEPES with the addition of fresh HEPES to 17 mM, and lipid (oleic acid, cholesterol, dipalmitic acid), 0.05–0.0625% BSA, 20 $\mu$g/ml L-cystine in 35-mm suspension culture dishes with the following growth factors: 4% FCS, 15% conditioned-medium from 5637 cells, 0.5–3% CHO conditioned-medium containing murine Kit ligand, 15 U/ml murine IL-3 from X63 Ag8-653 myeloma transfectant conditioned-media, 0.1–1 U/ml human erythropoietin, 100 µg/ml transferrin, 10 µg/ml bovine insulin (see ref. [25], and references therein for methods and suppliers of cytokines) along with increasing concentrations of SLT-1[26]. Cultures were incubated at 37° C. in a humidified atmosphere containing 5% $CO_2$ for 9–10 days. Colonies of greater than 50 cells were scored visually under the microscope and categorized morphologically. Results represent the mean of four 30-mm dishes plated with 30,000 nucleated murine cells each, in 1 ml. Mononuclear cells from the bone marrow of a patient with AML, obtained after informed consent, was plated in 35-mm Petri dishes. One ml of 0.8% methylcellulose containing $2\times10^5$ cells was supplemented with 10% 5637 conditioned medium, 20 U of erythropoietin, 10% conditioned medium from a CHO line expressing murine Kit ligand (Dr. Steven Clark, Genetics Institute, Cambridge, Mass.) and 50 U of human IL3. Plates were incubated in a humid atmosphere at 37° C. containing 5% $CO_2$ for the indicated periods of time. Colonies of greater than 50 cells were counted under a microscope.

Purification of CD34⁺ Cells, Cytotoxicity and Purging Assays

Human CD34+ cells (PBSC) were recovered from a G-CSF mobilized peripheral blood stem cell graft obtained by apheresis of a normal donor. They were purified to greater than 85% purity by depleting red blood cells using Ficoll banding. T-cells were depleted by sheep red blood cell resetting, and monocytes were removed by adherence to the plastic tissue culture plates after a 6-hour incubation. The remaining suspension cells were purified using anti-CD34 immunomagnetic beads (Dynal A. S.; Oslo, Norway) and a magnet. The $CD34^+$ cells were released from the beads using anti-anti-CD34F(Ab)s. Their purity and viability were verified by flow cytometry. These cells were then cultured in IMDM with 20% FCS for 2 days in the presence or absence of 1 µg/ml SLT-1, and their viability was measured by flow cytometry (light-scattering properties; 7-AAD dye exclusion). Simulated purging assays were carried out by co-culturing equal cell numbers of a human Burkitt's cell line, Daudi (CD 19⁺, CD77⁺), and CD34⁺ cells with or without SLT-1 (1 µg/ml) for 2 days. The viabilities of CD34⁺cells and the B-cell lymphoma (CD19⁺) were measured simultaneously by flow cytometry.

Immune Reconstitution Experiments

SCID mice (C.B-17 scid/scid)[27] were bred and maintained in a pathogen-free defined flora colony. Only female mice at 8–13 weeks of age were used for transplant experiments. Female BALB/c ByJ mice 6–8 weeks old were purchased from Jackson Laboratories (Bar Harbor, Me.) as a 'congenic' strain to SCID mice used as donors for the bone marrow transplants. All animal experiments were carried out according to the guidelines of the Medical Research Council of Canada. The holotoxin SLT-1 was purified from *E. coli* culture transformed with the SLT-1-coding plasmid[26]. Bone marrow was obtained from BALB/c ByJ mice and treated with or without 1 µg/ml SLT-1 for 1 h at 37° C. and washed. Bone marrow cells ($2\times10^6$) were injected into irradiated SCID mice. Ten weeks post-transplant, peripheral blood was obtained from the tail vein and analyzed for the presence of T-cells. Reconstitution of SCID mice with bone marrow from BALB/c ByJ mice was verified by flow cytometry analysis of 50 µl of peripheral blood from the reconstituted SCID mice, with untreated SCID mice and BALB/C ByJ mice as controls. The appearance of CD3-positive cells (mature T-cells) in the periphery was detected with an FITC-conjugated hamster anti-mouse T3 complex CD3ε monoclonal antibody (Cedarlane, Hornby, ON). Flow cytometry was performed on a Becton-Dickinson FACScan with Lysis II software. Data from 10,000 events (mononuclear cells) was collected.

SLT-1 Purging Experiments

The human Burkitt's lymphoma cell line, Daudi, was obtained from ATTC and was maintained in α-MEM with 20% heat-inactivated FCS (CELLect GOLD, ICN Flow). Bone marrow was isolated under aseptic conditions from the femora and tibiae of untreated SCID mice by flushing with a 25-gauge needle and IMDM media containing 5% FCS. Bone marrow was mixed 2:1 with or without Daudi cells, and treated with or without 10 ng/ml SLT-1 for 60 min in culture dishes at 37° C. Cells were washed twice in Hanks' balanced salt solution (without $CaCl_2$ and $MgCl_2$) supplemented with 1% FCS and resuspended in Hanks/FCS solution so that each mouse received $2\times10^6$ nucleated bone marrow cells with or without $1\times10^6$ viable (dye-excluding) Daudi cells in 200–300 µl. Cells were mixed and split into equal volumes for the various treatment groups so that the mice received an equal number of cells. SCID mice received a sublethal dose of γ-irradiation (0.4 Gy) from a $^{137}Cs$ source (dose rate=0.54 Gy/min) just prior to injection of the bone marrow[28]. Mice were monitored daily for signs of disease. Animals were euthanized at signs of paralysis and the time recorded.

Screening of Human Cancers for SLT-1 Receptors by Flow Cytometry

The B-subunit of SLT-1 was purified from an *E. coli* culture transformed with the B-subunit-coding plasmid, pJLB122, as previously described[29]. Fluorescein isothiocyanate (FITC; Molecular Probes, Eugene, Oreg.) was added directly to purified SLT-B dissolved in PBS, pH 7.4. Free FITC was removed by chromatography on a Sephadex G-50 (Pharmacia) column equilibrated in 50 mM $NH_4HCO_3$. The orange-colored peak eluting in the void volume of the column was collected, lyophilized and stored at −5° C. The FITC-SLT-B conjugate was resuspended to a concentration of 0.25 mg/ml in PBS or water. Samples were stained with a 1:50 to 1:75 dilution of FITC-SLT-B and analyzed by flow cytometry using a Becton-Dickinson FACScan flow cytometer. Patient sample diagnosis were based on several criteria including histology, cytogenetics and was made by a pathologist in the group (BP).

REFERENCES

1. O'Brien, A. D., et al. Shiga toxin: biochemistry, genetics, mode of action, and role in pathogenesis. Curr. Top. Micro. Immunol. 180, 65–94 (1992).
2. Hofmann, S. L. Southwestern internal medicine conference: Shiga-like toxins in hemolytic-uremic syndrome and thrombotic thrombocytopenic purpura. Am. J. Med. Sci. 306, 398–406 (1993).
3. Murray, L. J., Habeshaw, J. A., Wiels, J. & Greaves, M. F. Expression of Burkitt lymphoma-associated antigen (defined by the monoclonal antibody 38.13) on both normal and malignant germinal-centre B cells. Int. J. Cancer 36, 561–565 (1985).
4. Mangeney, M., Richard, Y., Coulaud, D., Tursz, T. & Wiels, J. CD77: an antigen of germinal center B cells entering apoptosis. Eur. J. Immunol. 21, 1131–1140 (1991).
5. Schwartz-Albiez, R., et al. Neutral glycosphingo-lipids of the globo-series characterize activation stages corresponding to germinal center B cells. Int. Immunol. 2, 929–936 (1990).
6. Oosterwijk, E., Kalisiak, A., Wakka, J. C., Scheinberg, D. A. & Old, L. J. Monoclonal antibodies against Galα

1-4Galβ 1-4Glc (P$^k$, CD77) produced with a synthetic glycoconjugate as immunogen: reactivity with carbohydrates, with fresh frozen human tissues and hematopoietic tumors. Int. J. Cancer 48, 848–854 (1991).
7. Kalisiak, A., Minniti, J. G., Oosterwijk, E., Old, L. J. & Scheinberg, D. A. Neutral glycosphingolipid expression in B-cell neoplasms. Int. J. Cancer 49, 837–845 (1991).
8. Taga, S., Mangeney, M., Tursz, T. & Wiels, J. Differential regulation of glycosphingolipid biosynthesis in phenotypically distinct Burkitt's lymphoma cell lines. Int. J. Cancer 61, 261–267 (1995).
9. Horning, S. J. Natural history of and therapy for the indolent non-Hodgkin's lymphomas. Semin. Oncol. 20, 75–88 (1993).
10. Brinkmann, U. & Pastan, I. Immunotoxins against cancer. Biochim. Biophys. Acta 1198, 27–45 (1994).
11. Ghetie, V. & Vitetta, E. Immunotoxins in the therapy of cancers: from bench to clinic. Pharmac. Ther. 63, 209–234 (1994).
12. Gottstein, C., Winkler, U., Bohlen, H., Diehl, U. & Engert, A. Immunotoxins: is there a clinical value? Ann. Oncol. 5, S97–S103 (1994).
13. Vallera, D. A. Immunotoxins: will their clinical promise be fulfilled? Blood 83, 309–317 (1994).
14. Ghetie, M.-A., et al. Antitumor activity of Fab' and IgG-anti-CD22 immunotoxins in disseminated human B lymphoma grown in mice with severe combined immunodeficiency disease: effect on tumor cells in extranodal sites. Cancer Res. 51, 5876–5880 (1991).
15. Vitetta, E. S. From the basic science of B cells to biological missiles at the bedside. J. Immunol. 153, 1407–1420 (1994).
16. Brodin, N. T., et al. Monoclonal antibodies produced by immunization with neoglycoproteins containing Galα 1-4Galβ1-4Glcβ-O and Galα 1-4Galβ 1-4GlcNAcβ-O residues: useful immunochemical and cytochemical reagents for blood group P antigens and a differentiation marker in Burkitt lymphoma and other B-cell malignancies. Int. J. Cancer 42, 185–194 (1988).
17. Cohen, A., et al. Expression of glycolipid receptors to Shiga-like toxin on human B lymphocytes: a mechanism for the failure of long-lived antibody response to dysenteric disease. Int. Immunol. 2, 1–8 (1990).
18. Carroll, A. M., Hardy, R. R. & Bosma, M. J. Occurrence of mature B (IGM$^+$, B220$^+$) and T (CD3$^+$) lymphocytes in scid mice. J. Immunol. 143, 1087–1093 (1989).
19. Matsumoto, K., et al. Cell counts in peripheral blood and bone marrow of male C.B-17 scid/scid mice. Lab. Animals 29, 218–222 (1995).
20. Wiels, J., Mangeney, M., Tetaud, C. & Tursz, T. Sequential shifts in the three major glycosphingolipid series are associated with B cell differentiation. Int. Immunol. 3, 1289–1300 (1991).
21. Gordon, J., et al. Phenotypes in chronic B-lymphocytic leukemia probed by monoclonal antibodies and immunoglobulin secretion studies: identification of stages of maturation arrest and the relation to clinical findings. Blood 62, 910–917 (1983).
22. Pudymaitis, A. & Lingwood, C. A. Susceptibility to verotoxin as a function of the cell cycle. J. Cell. Physiol. 150, 632–639 (1992).
23. Ghetie, M.-A., Vitetta, E. S. Recent developments in immunotoxin therapy. Curr. Opin. Immunol. 6, 707–714 (1994).
24. Scheuermann, R. H. & Racila, E. CD19 antigen in leukemia and lymphoma diagnosis and immunotherapy. Leuk. Lymph. 18, 385–397 (1995).
25. Trevisan, M. & Iscove, N. N. Phenotypic analysis of murine long-term hemopoietic reconstitutive cells quantitated competively in vivo and comparison with more advanced colony-forming progeny. J. Exp. Med. 181, 93–104 (1995).
26. Petric, M., Karmali, M. A., Richardson, S. & Cheung, R. Purification and biological properties of Escherichia coli verocytotoxin. FEMS Microbiol. Lett. 41, 63–68 (1987).
27. Bosma, G. C., Custer, R. P. & Bosma, M. J. A severe combined immunodeficiency mutation in the mouse. Nature 301, 527–530 (1983).
28. Fulop, G. M. & Phillips, R. A. Full reconstitution of the immune deficiency in scid mice with normal stem cells requires low-dose irradiation of the recipients. J. Immunol. 136, 4438–4443 (1986).
29. Ramotar, K., et al. Characterization of Shiga-like toxin-1 B-subunit purified from overproducing clones of the SLT-1 B cistron. Biochem. J. 272, 805–811 (1990).
30. Boyd, B., Richardson, S. & Gariepy, J. Serological responses to the B subunit of Shiga-like toxin-1 and its peptide fragments indicate that the B subunit is a vaccine candidate to counter the action of the toxin. Infect. Immun. 59, 750–757 (1991).

I claim:

1. A method for the selective ex vivo purging of CD77 positive cells from a population of mammalian hematopoietic cells, comprising the steps of:

harvesting hematopoietic cells from a mammal expressing CD77$^+$ cells; and treating the hematopoietic cells with lethal dose of unconjugated shiga-toxin or shiga-like toxin-1 for a sufficient time to kill the CD77$^+$ cells, such that CD77$^+$ cells are purged from the population of mammalian hematopoietic cells.

2. A method as claimed in claim 1, wherein the CD77 positive cells are a non-Hodgkin's lymphoma.

3. A method as claimed in claim 1, wherein the lethal dose of toxin is 10 ng/ml applied at 37° C. for about 1 hour.

4. The method of claim 1, further comprising washing the hematopoietic cells to remove residual shiga toxin or shiga-like toxin-1.

5. The method of claim 4, wherein the washing is performed using Hanks' balanced salt solution without CaCl$_2$ and MgCl$_2$, but supplemented with 1% FCS.

6. A method as claimed in claim 5, wherein the washing is performed twice.

7. A method as claimed in claim 1, wherein the mammal is a human.

8. A method for the selective ex vivo purging of CD77 positive cells from a population of mammalian hematopoietic cells, comprising the steps of:

harvesting hematopoietic cells from a mammal expressing CD77$^+$ cells;

contacting the cells in suspension with a resin having at least the B-subunit of shiga toxin attached thereto, so that the CD77$^+$ cells are bound via the subunit to the resin; and separating the unbound hematopoietic cells from the resin.

9. A method as claimed in claim 8, wherein the CD77$^+$ cells are a non-Hodgkin's lymphoma.

10. A method as claimed in claim 8, wherein the mammal is a human.

11. A method for the treatment of a cancer consisting of a non-Hodgkin's lymphoma in humans, comprising the steps of:

harvesting hematopoietic cells from a human having the lymphoma;

treating the harvested cells with a lethal dose of unconjugated shiga toxin or shiga-like toxin-1 for a sufficient time to kill the cancer cells;

washing the treated hematopoietic cells to remove residual toxin;

irradiating the human to destroy cancer cells in vivo; and transplanting the treated hematopoietic cells into the irradiated human so that the human's immune system is reconstituted.

\* \* \* \* \*